United States Patent
Hall et al.

(10) Patent No.: US 8,848,861 B2
(45) Date of Patent: Sep. 30, 2014

(54) SYSTEM FOR MEDICAL IMAGING USING LONG PERSISTENCE CONTRAST AGENTS

(75) Inventors: Andrew F Hall, St. Charles, MO (US); Jan Boese, Eckental (DE)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 337 days.

(21) Appl. No.: 13/484,311

(22) Filed: May 31, 2012

(65) Prior Publication Data

US 2012/0307964 A1 Dec. 6, 2012

Related U.S. Application Data

(60) Provisional application No. 61/493,662, filed on Jun. 6, 2011.

(51) Int. Cl.
*A61B 6/00* (2006.01)
*A61B 6/03* (2006.01)

(52) U.S. Cl.
CPC .................. *A61B 6/481* (2013.01); *A61B 6/504* (2013.01); *A61B 6/03* (2013.01); *A61B 6/541* (2013.01); *A61B 6/503* (2013.01)
USPC ............................... 378/8; 600/428; 600/431

(58) Field of Classification Search
CPC .......... A61B 6/03; A61B 6/481; A61B 6/541; A61B 6/504; A61B 6/503
USPC .................. 378/4–20; 600/420, 425, 428, 431
See application file for complete search history.

(56) References Cited

U.S. PATENT DOCUMENTS 4,031,884 A * 6/1977 Henzel .......................... 600/431

OTHER PUBLICATIONS

Christopher Rohkohl, Gunter Lauritsch, Marcus Prummer, and Joachim Hornegger, "Interventional 4-D Motion Estimation and Reconstruction of Cardiac Vasculature without Motion Periodicity Assumption", Medical Image Computing and Computer-Assisted Intervention—MICCAI 2009 Lecture Notes in Computer Science, 2009, vol. 5761/2009, 132-139, DOI: 10.1007/978-3-642-04268-3_17.

Ahmad Bitarafan, et al., "Respiratory Motion Detection and Correction in ECG-Gated SPECT: a New Approach", Korean J Radiol. Nov.-Dec. 2008; 9(6): 490-497.

Bruce V. Bigelow, "Marval Biosciences, San Diego's Latest Virtual Biomedical Startup, Raises $2.5M to Develop Next-Generation Contrast Agents for Medical Imaging", website http://www.xconomy.com/san-diego/2009/10/02/marval-biosciences-san-diego%e2%80%99s-latest-virtual-biomedical-startup-raises-2-5m-to-develop-next-generation-contrast-agents-for-medical-imaging/, printed on May 22, 2012.

* cited by examiner

*Primary Examiner* — Courtney Thomas
(74) *Attorney, Agent, or Firm* — Brennan K Bradley (57) ABSTRACT

A system acquires images in the presence of a contrast agent of relatively long persistence using a synchronization processor, image acquisition device and imaging controller. The synchronization processor provides an image acquisition trigger signal for acquiring images at a particular point within both a cardiac and a respiratory cycle in response to signals representing cardiac and respiratory cycles. The image acquisition device includes an assembly comprising a radiation emitter and detector rotatable about a patient for acquiring images of a portion of patient anatomy at different angles. The imaging controller initiates acquisition of data representing multiple images in the presence of a contrast agent of relatively long persistence by repetitively, initiating rotation of the assembly to an angle, acquiring an image at the angle in response to the trigger signal and incrementally increasing the angle.

16 Claims, 8 Drawing Sheets

SYSTEM FOR MEDICAL IMAGING USING LONG PERSISTENCE CONTRAST AGENTS

This is a non-provisional application of provisional application Ser. No. 61/493,662 filed Jun. 6, 2011, by A. Hall et al.

FIELD OF THE INVENTION

This invention concerns a system for tomographic imaging of the human body, and more specifically to diagnostic imaging using a long-persistence contrast agent.

BACKGROUND OF THE INVENTION

Coronary artery disease (CAD) is characterized by a narrowing of a section of the coronary artery tree, which supplies blood to the heart. The narrowing is caused by atherosclerotic plaques, which impair blood flow through the arteries. The lack of blood flow to the heart, caused by this condition, can eventually result in a myocardial infarction, or heart attack. Over 13 million people in the US have CAD. It is the leading cause of death in the US, claiming over 1.4 million lives each year. Approximately 6 million patients arrive in US hospital emergency rooms annually with chest pain. The hospital staff need to quickly determine whether a patient is suffering from a CAD induced attack. A diagnostic coronary angiogram is used to determine whether or not to perform surgery (coronary bypass), or an interventional procedure (e.g., insertion of a stent), to open a narrowed artery. Methods for creating a diagnostic image of the coronary arteries include, use of two-dimensional X-ray angiography and three-dimensional CT angiography. The determination of "diagnostic quality" in an image is achieved by being able to identify coronary lesions (narrowings) with a high degree of sensitivity and specificity.

In 2D X-ray angiography, a patient needs to have a catheter inserted into an artery near the groin. The catheter is navigated through the arterial system to the ostium of a coronary artery, under the guidance of an X-ray angiography system. A contrast agent is injected directly into the coronary artery, via the catheter, while the X-ray angiography system records a rapid (~30 fps) sequence of images of the opacified artery tree. This two-dimensional image sequence (or Cine angiogram) normally includes the entire artery tree. Cine angiograms are often taken at other X-ray tube-detector angulations to acquire additional views of the artery tree, to help overcome limitations inherent in using a two-dimensional image to examine a three dimensional object.

Coronary angiography suffers from several limitations. The X-ray systems used are relatively expensive. Access to a patient arterial system (to place the catheter) is required (increasing the risk of complication), and known typical contrast agents can further harm compromised kidneys, in some cases resulting in kidney failure. Further, a procedure requires a physician (interventional cardiologist) and other staff members (two or more) to gain arterial access, run the angiography system and care for a patient. Intra-procedure 3D imaging (i.e. that is performed during an interventional procedure, rather than before or after the interventional procedure) uses C-arm CT (computed tomography), whereby a C-arm of the angiography system (which contains both the X-ray tube and detector), rotates around the patient while capturing a series of images at closely spaced angulations. The acquired images are used to create a three-dimensional image of patient anatomy (including vessels, if contrast agent is injected). A limitation in use of C-arm CT is temporal resolution. (1 rotation per 5 seconds) Methods to image coronary arteries with C-arm CT include use of multiple rotations with retrospective cardiac gating as well as use of a single C-arm rotation, together with a motion compensation process in image reconstruction. These known methods fail to provide diagnostic image quality.

Computed Tomography (CT) Angiography enables capture of coronary images of diagnostic quality using scanners that rotate at high speeds and with high numbers of radiation detector rows (up to 320, which increases the amount of anatomy that can be imaged in a single rotation). CT systems capable of diagnostic image quality are expensive and CT has the same risks in use of contrast agent as angiography systems. CT also may lack reliability in capturing images during administration of a bolus of contrast agent as it moves through coronary arteries and an image may need to be captured during a single phase of a cardiac cycle in a window of several milliseconds. Further, both Angiography and CT use radio-opaque (iodinated) contrast agent to illuminate vessels for X-ray imaging. This agent is usually delivered as a bolus and is cleared rapidly by the kidneys, such that the only opportunity to image the area-of-interest is during a "first pass" of contrast agent through that area. Furthermore, since the contrast bolus moving through the vessels is a dynamic event, the time (relative to the start of contrast injection) when the image needs to be acquired is not always predictable, and the contrast agent does not always completely mix with the blood, and can cause artifacts in acquired X-ray images (both 2D and 3D). The limitations of iodinated contrast agents have resulted in the development of sophisticated and expensive imaging systems, for both angiography and CT, which are designed to capture images quickly, as the contrast agent rapidly moves through the blood vessels to be imaged. These systems are required to be fast because of the short life of contrast agent in the vessels, and the motion of the beating heart. A system according to invention principles addresses these deficiencies and related problems

SUMMARY OF THE INVENTION

A system uses the long half-life property of long persistence contrast agents to facilitate use of patient ECG and respiration signals to trigger image acquisition at a particular state of a heart cycle and reduce mechanical and electrical imaging system hardware and associated complexity required, to produce diagnostic quality 3D images of coronary arteries, for example. A system acquires images in the presence of a contrast agent of relatively long persistence using a synchronization processor, image acquisition device and imaging controller. The synchronization processor provides an image acquisition trigger signal for acquiring images at a particular point within both a cardiac and a respiratory cycle in response to signals representing cardiac and respiratory cycles. The image acquisition device includes an assembly comprising a radiation emitter and detector rotatable about a patient for acquiring images of a portion of patient anatomy at different angles. The imaging controller initiates acquisition of data representing multiple images in the presence of a contrast agent of relatively long persistence by repetitively, initiating rotation of the assembly to an angle, acquiring an image at the angle in response to the trigger signal and incrementally increasing the angle.

DETAILED DESCRIPTION OF THE INVENTION

A three-dimensional X-ray imaging system according to invention principles advantageously uses the long half-life property of long persistence contrast agents to reduce mechanical and electrical imaging system hardware and associated complexity required to produce diagnostic quality 3D images of coronary arteries, for example. The long-half life of the contrast agent enables the system to use patient ECG and respiration signals to trigger image acquisition over an extended time period when the heart is in the same state of a heart cycle. Such image acquisition at a particular phase of a patient heart cycle over an extended time period is unachievable with typical short persistence contrast agents.

A class of long persistence contrast agents, such as a liposome encapsulated contrast agent, advantageously provides a long circulating life (i.e. they are not quickly removed from the blood stream by the kidneys), and may not be substantially removed by the kidneys at all, but rather by the liver. A long half-life contrast agent circulates in the body, substantially at its original concentration, for 24 hours or longer, although this concentration is somewhat less than a bolus of 100% contrast moving through a vessel, as is the case with 2D coronary angiography.

Figure 1:
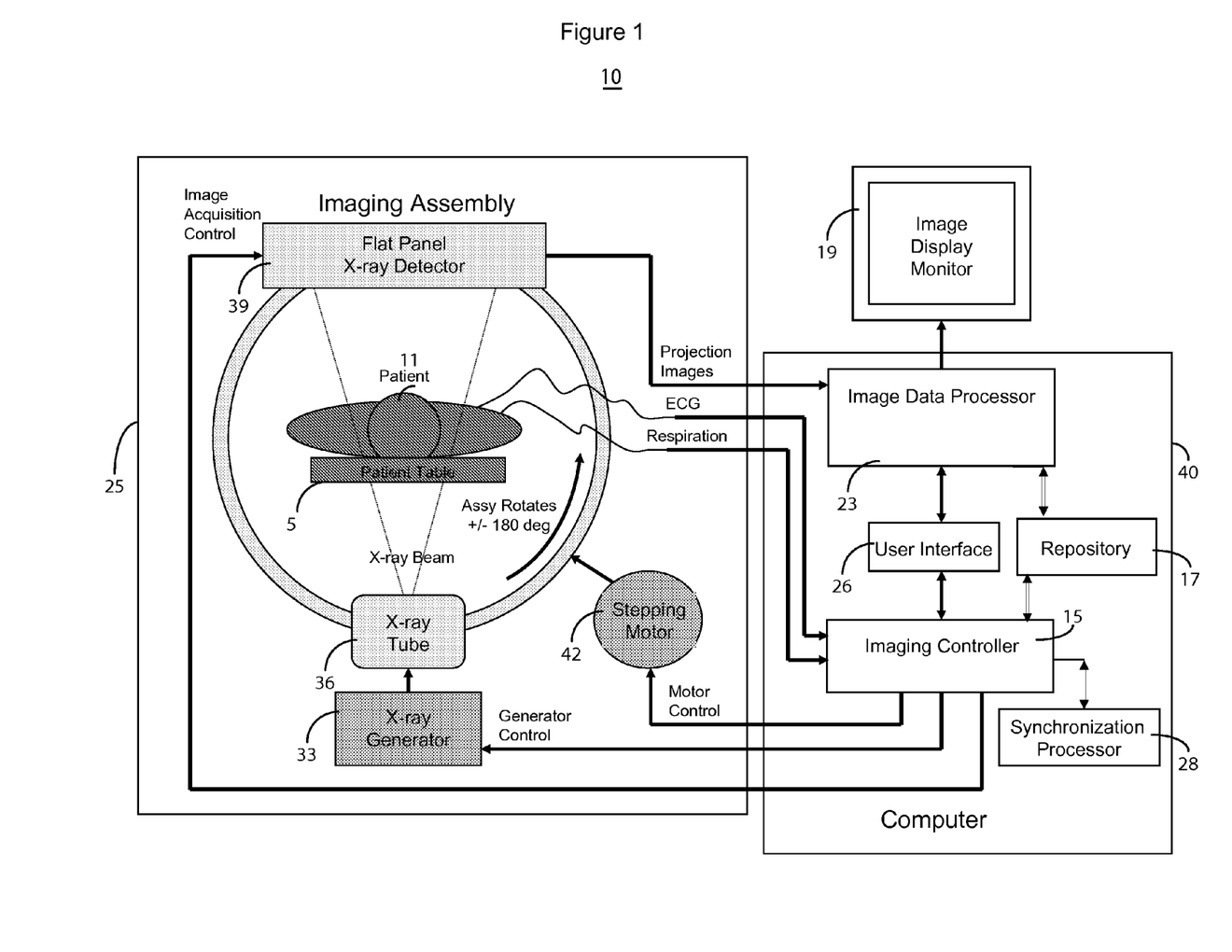
FIG. 1 shows a system for acquiring images in the presence of a contrast agent of relatively long persistence, according to invention principles.

FIG. 1 shows system 10 for acquiring images in the presence of a contrast agent of relatively long persistence. System 10 includes Computed Tomography (CT) imaging system 25 including a rotating X-ray imaging assembly comprising a radiation detector 39 and emitter 36, an X-ray generator 33 and a motor 42 to rotate the imaging assembly relatively slowly compared to a known high speed X-ray C-arm or CT imaging system used in contrast agent imaging. Such known imaging systems use conventional short persistence contrast agents. System 10 also employs display 19 and at least one computer 40 including image data processor 23, user interface 26, imaging controller 15 including ECG and respiration sensor devices coupled to patient 11 on patient table 5, repository 17 and synchronization processor 28. Any of the units within at least one computer 40 may include one or more of the other units within computer 40. Alternatively they may reside in another unit on a network linking the system 10 units.

Computer 40 (e.g. a processing device such as one or more workstations, computers or portable devices such as notebooks, Personal Digital Assistants, phones) includes a user interface 26 enabling user interaction with a Graphical User Interface (GUI) and display 19 supporting GUI and medical image presentation in response to predetermined user (e.g., physician) specific preferences. A medical image study individually includes multiple image series of a patient anatomical portion which in turn individually include multiple images. Imaging device 25 acquires multiple sequential X-ray projection images of a vessel structure in the presence of a contrast agent in a 3D volume of interest. At least one repository 17 stores 2D image data representing a 2D DSA X-ray image sequence through the imaging volume in the presence of a contrast agent.

The rotating X-ray imaging assembly comprises a flat panel detector 39, an X-ray radiation tube 36 and a frame that fixes the relationship of the tube and detector, and allows the assembly to rotate around the patient, such that the control and power cables do not need to be connected by slip rings, as is required for CT scanners. A patient 11 is located and initially positioned on a patient support table 5 in a measuring field between X-ray tube 36 and X-ray radiation detector 39 opposite the tube across the CT imaging unit bore, while the X-ray tube 36 and the detector 39 move in a fashion rotating about the patient 11. CT system 25 supports different scanning modes but advantageously in one embodiment only requires a 200 degree range of rotation to acquire a 3D dataset, for example, for imaging patient 11. X-ray tube 36 may comprise a single X-ray tube or multiple X-ray tubes (to accelerate image acquisition) with detector 39 lying opposite for scanning.

In order to control the CT system 25 and to evaluate the detector data received, computer programs (machine readable instructions) are executed by imaging controller 15 to perform methods supporting operation of system 25 and control Imaging Assembly rotation, X-ray generation and image acquisition. The programs are stored in memory of repository 17. Display 19 presents output data provided by the system. Synchronization processor 28 provides an image acquisition trigger signal for acquiring images at a particular point within both a cardiac and a respiratory cycle in response to signals representing cardiac and respiratory cycles acquired from patient 11. CT system 25 acquires images of a portion of patient anatomy at different angles. Imaging controller 15 initiates acquisition of data representing multiple images in the presence of a contrast agent of relatively long persistence by repetitively, initiating rotation of the assembly to an angle, acquiring an image at the angle in response to the trigger signal and incrementally increasing the angle. User interface control device 26 comprises a keyboard, mouse, touchscreen or voice data entry and interpretation device, for example. CT system 25 (or in another embodiment an X-ray) modality imaging system provides patient medical images. The medical images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images.

Figure 2:
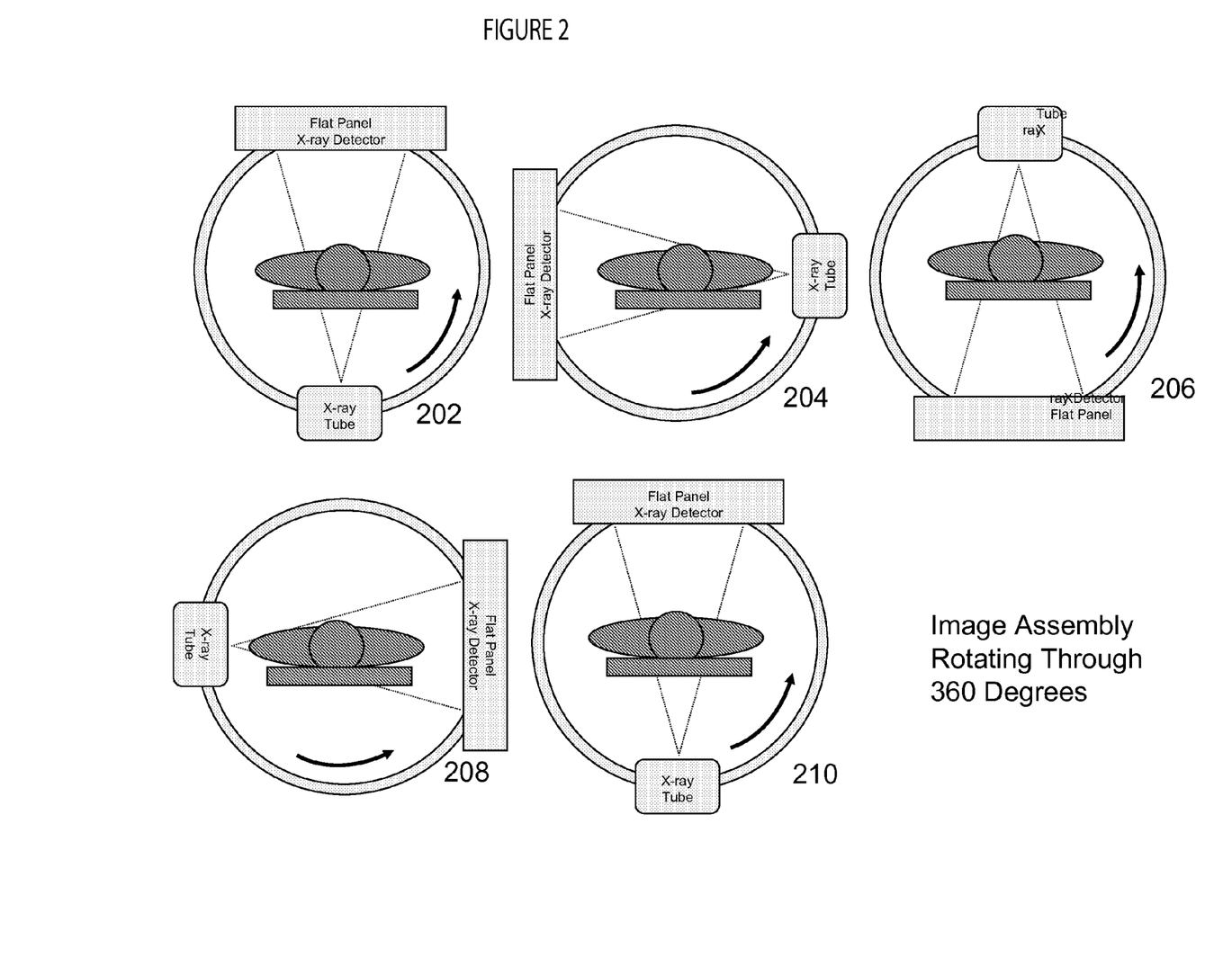
FIG. 2 shows an imaging system radiation source and flat-panel detector assembly (similar to that used for C-arm CT) and rotational imaging positions in a 360 degree range.

FIG. 2 shows a Computer Tomography (CT) imaging system radiation source and detector assembly showing rotational imaging positions 202, 204, 206, 208 and 210 in a 360 degree range. During the scanning of a patient, the Imaging Assembly, under the control of the computer 40, rotates up to 360 around the patient, capturing images at regular angular intervals. The minimum rotation required for accurate 3D image reconstruction is 180 degrees, plus an X-ray beam or detector width, but 360 degrees provides higher image quality. X-ray electrical generator 33 provides high voltage electrical power to X-ray tube 36 under control of imaging controller 15. Generator 33 provides short pulse widths to capture motion of the heart with minimal blurring. Stepping motor 42 rotates the Imaging Assembly around the patient under direction of imaging controller 15. System 10 advantageously employs an X-ray tube of reduced complexity relative to a known CT system rotating anode X-ray angiography tube as it omits use of a heat dissipating rotor since a required radiation emission pulse rate is typically lower in response to use of a long persistence contrast agent. The system in one embodiment advantageously eliminates a need for active cooling (i.e. no closed system oil filled x-ray chamber is needed). In one embodiment, system 10 employs a radiation emission pulse rate of approximately one pulse per second, for example, rather than 30 pulses per second for known typical angiography systems. The system uses a fixed anode X-ray tube 36 and a flat-panel X-ray detector comprising a standard angiography detector of reduced complexity and cost with reduced image data read-out rate requirements. The system 10 imaging assembly frame allows repeatable rotation and in one non-C-arm embodiment offers enhanced repeatability compared to C-arm systems, as the imaging system is not mounted to a C-arm, which is a less stable mechanical structure. Furthermore, unlike a conventional CT system, imaging system 25 (FIG. 1) may be open to prevent patient claustrophobia.

Figure 3:
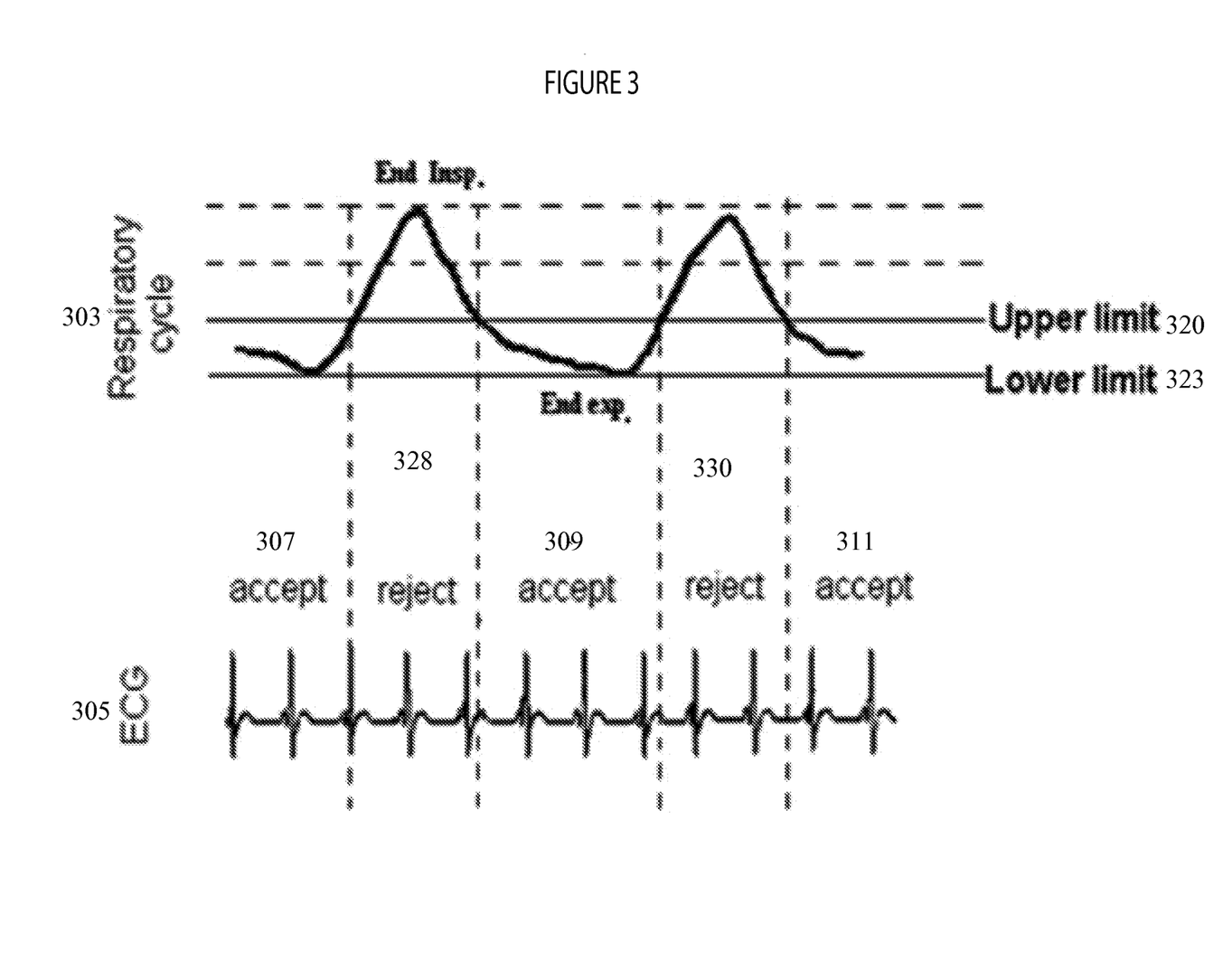
FIG. 3 shows respiration and heart rate triggering of imaging with reduced rate imaging assembly rotation and using a long persistence contrast agent, according to invention principles.

In operation, a patient lying supine on a patient support table breathing normally, is injected in a peripheral vein with a long half-life, long persistence contrast agent. The Imaging Assembly is controlled by the Imaging controller 15 in computer 40 such that a series of angularly spaced images and regular angle increments is acquired and sent to an image data processor 23 for image reconstruction. FIG. 3 shows respiration and heart rate triggering of imaging in response to respiratory signal 303 and ECG signal 305, with reduced rate imaging assembly rotation and using a long persistence contrast agent. Imaging controller 15 initiates acquisition of images in response to ECG signal 305 and respiratory signal 303 derived from patient 11. For each imaging angle, imaging controller 15 initiates acquisition of an image in response to the heart being in a pre-determined phase of the cardiac cycle (e.g. end systole), and being concurrently in a pre-determined phase of the respiratory cycle (e.g., end expiration) comprising a portion of signal 303 between thresholds 320 and 323. Thereby imaging controller 15 initiates acquisition of images in respiratory and ECG signal portions 307, 309 and 311 and excludes acquisition in portions 328 and 330.

For a heart rate of 60 beats per minute (bpm), a respiration rate of 10 respirations per minute (rpm), and with 50% of heart beats in the end-expiration window (307, 309, 311), the system acquires 600 images in 20 minutes. In order to capture 600 images over 360 degrees in 20 minutes, the imaging assembly rotates at an average rate of 18 degrees per minute (0.3 degrees per second), and a maximum rate of 36 degrees per minute (0.6 degrees/second). The average X-ray pulse rate in this example is advantageously reduced to 0.5 pulses per second. Imaging controller 15 initiates acquisition of an image in response to occurrence of this condition and directs the Imaging Assembly to move to a next angular position. This is repeated until the system has rotated through the complete 360 degrees around patient 11. Known systems fail to perform such a long duration image acquisition which may take 15-30 minutes, for example, since images need to be acquired while a short half-life contrast agent bolus moves through vessels in response to a single contrast bolus injection. During the time required to acquire the projection images, the patient may become restless and shift slightly, normally to the right or left. Radio-opaque fiducial markers are applied to the patient's skin, or to a similar location. The fiducial markers are seen in the projection images (normally above or below the target anatomy), and the system shifts images relatively to compensate for patient motion, prior to image reconstruction.

Figure 4:
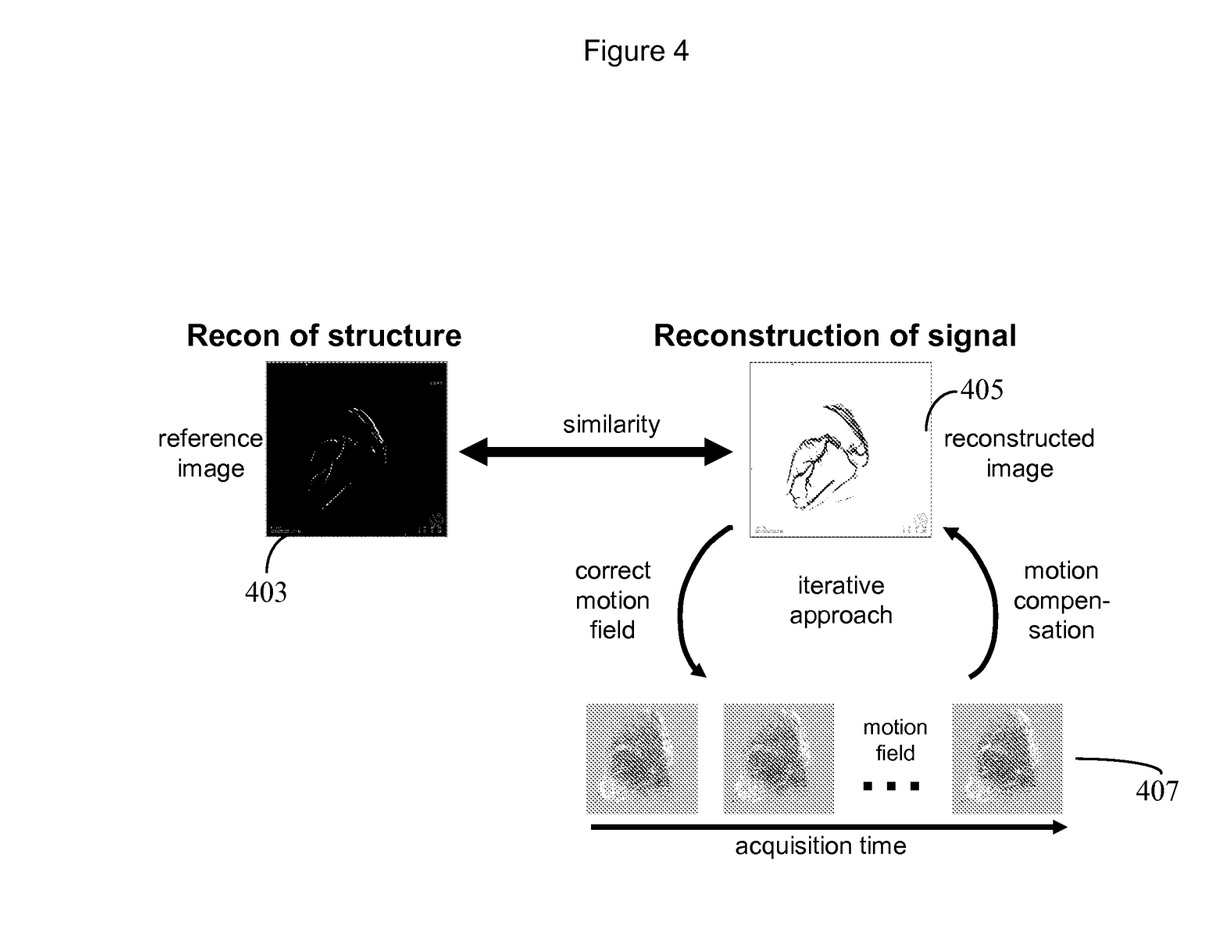
FIG. 4 shows a motion correction method used in image processing post-acquisition to provide corrected images, according to invention principles.

FIG. 4 shows a motion correction method used in image processing post-acquisition to provide corrected images by image data processor 23. Processor 23 includes an image reconstruction processor that processes an acquired group of images captured under similar heart and respiratory cycle phase conditions as if the heart were substantially stationary during image acquisition. However, the heart does not beat exactly the same way twice, and a patient typically does not breathe exactly the same way twice. Therefore, there are minor changes in both the location and deformation of the vessels in the group of images. This may cause artifacts during image reconstruction that are corrected by using image motion compensation. The image motion compensation compensates for minor variations using a motion compensation processor (contained within the Image Reconstruction processor of processor 23) to account for this motion and reduces the artifacts. In one embodiment a known motion compensation function is used as described by Rohkohl et al., in Medical Image Computing and Computer Assisted Intervention MICCAI, London, UK, Sep. 20-24, 2009. Processor 23 compares a selected reference image 403 with individual images of sequence 407 to determine corresponding individual motion compensation vectors for correcting the individual images to provide motion compensated reconstructed images such as image 405. Reference image 403 is acquired using ECG and respiratory signal triggering to acquire the image with known patient position.

Alternatively, the system may use another known motion compensation processor that derives an initial motion estimate, makes changes to the motion field, evaluates the results, and iterates until the image is stable and optimized as determined by an error reduction indicative metric. Data capture in one embodiment is iterative and multiple images are acquired at a particular body location, and processed using the motion compensation function to determine the best image and the resulting image is sent to a display monitor.

Figure 5A:
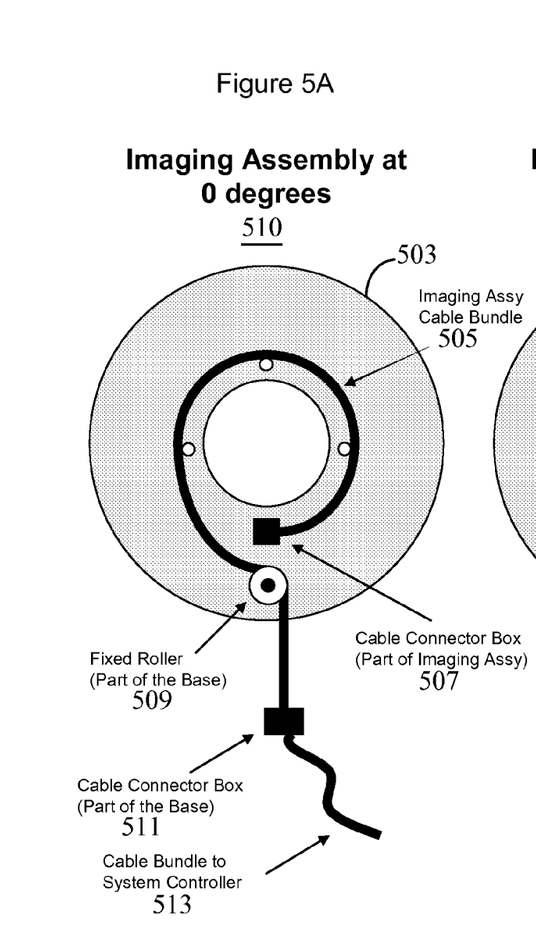
FIGS. 5A, 5B and 5C show a CT or X-ray C-arm radiation source and detector assembly system providing reduced rate and constrained range rotation, according to invention principles.
Figure 5B:
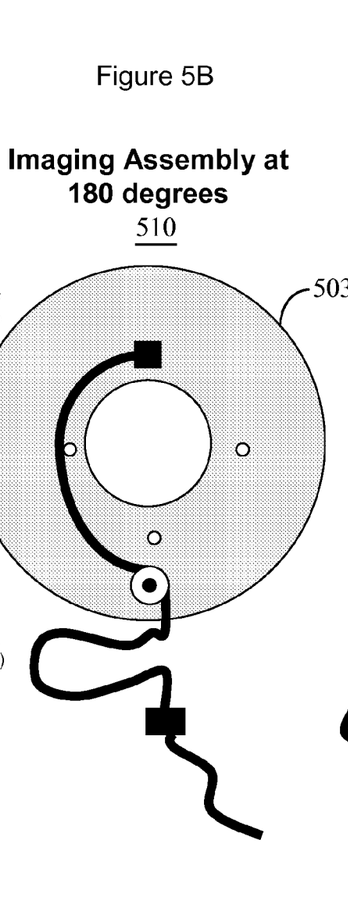
Figure 5C:
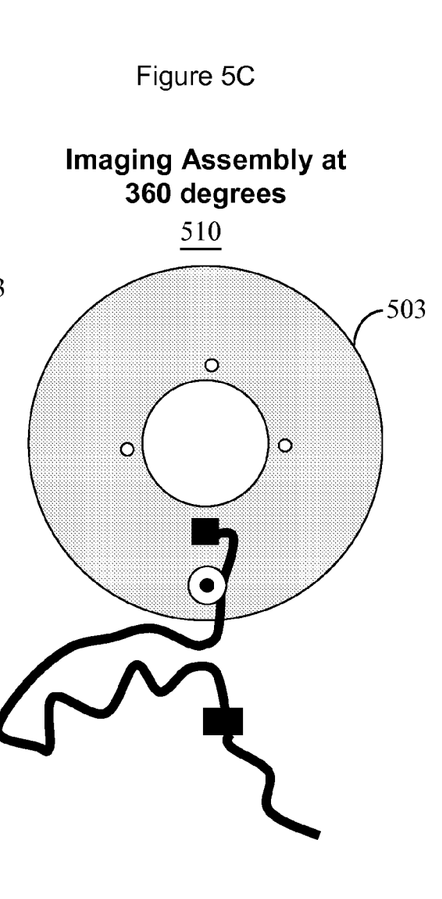

FIGS. 5A, 5B and 5C show a CT or X-ray C-arm radiation source and detector assembly 503 at zero, 180 and 360 degrees of angular rotation in a system 510 providing reduced rate and constrained range rotation. Assembly 503 is rotatable about a patient for acquiring images of a portion of patient anatomy at different angles. A motor rotates assembly 503 at less than one degree per second over a fixed range substantially comprising at least 360 degrees. In one constrained range embodiment using an X-ray system type flat detector, rotation is constrained to 180 degrees plus the width of a radiation detector providing a total of about 200 degrees rotational range. However image quality may be improved at the cost of providing more rotational range in a further constrained range embodiment providing 360 degrees maximum range, for example.

An extendible and retractable cable 505, fixed roller 509, cable connector boxes 507, 511 and cable bundle controller 513 enable rotation of the assembly over a fixed range substantially comprising at least 360 degrees. The reduced capability motor and cable system have increased reliability, less complex design with fewer parts and reduced cost relative to typical known CT and Angiography systems providing comparable imaging performance. The system is readily usable by Emergency Departments, Clinics and physician offices and because the long persistence contrast agent is injected peripherally, the procedure is easily performed by a nurse or radiology technician, without need for a physician (i.e. no femoral or radial artery access required).

Figure 6:
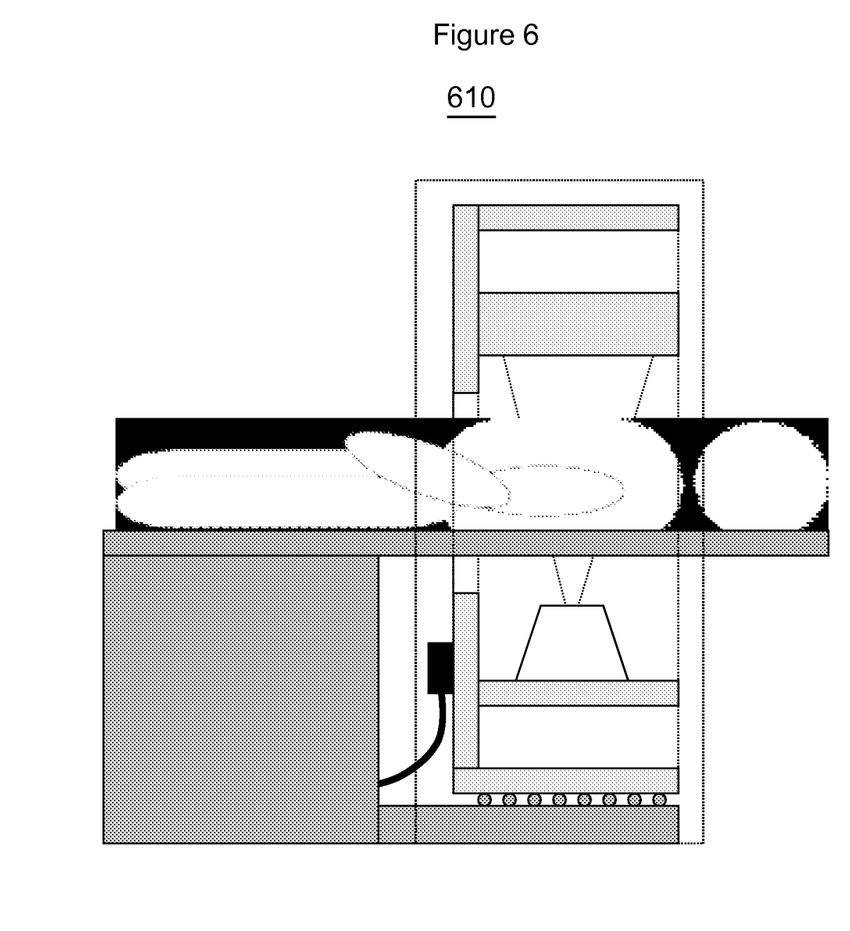
FIG. 6 shows a reduced complexity CT imaging system providing reduced rate and constrained range rotation, according to invention principles.

FIG. 6 shows reduced complexity CT imaging system 610 providing reduced rate and constrained range rotation. System 610 differs from a known corresponding CT scanner in speed and cable management and rotates the imaging assembly at less than 1 degree/sec advantageously using a reduced cost, reduced complexity and component count imaging rotation assembly. In one embodiment, system 610 advantageously requires no slip rings for conveying power and signals from a base to an imaging assembly including radiation detector and source using a fixed cable assembly with a 360 maximum rotation (i.e. non-continuous rotation). The system reduced complexity makes the system affordable by clinics and offices, not just hospitals.

Figure 7:
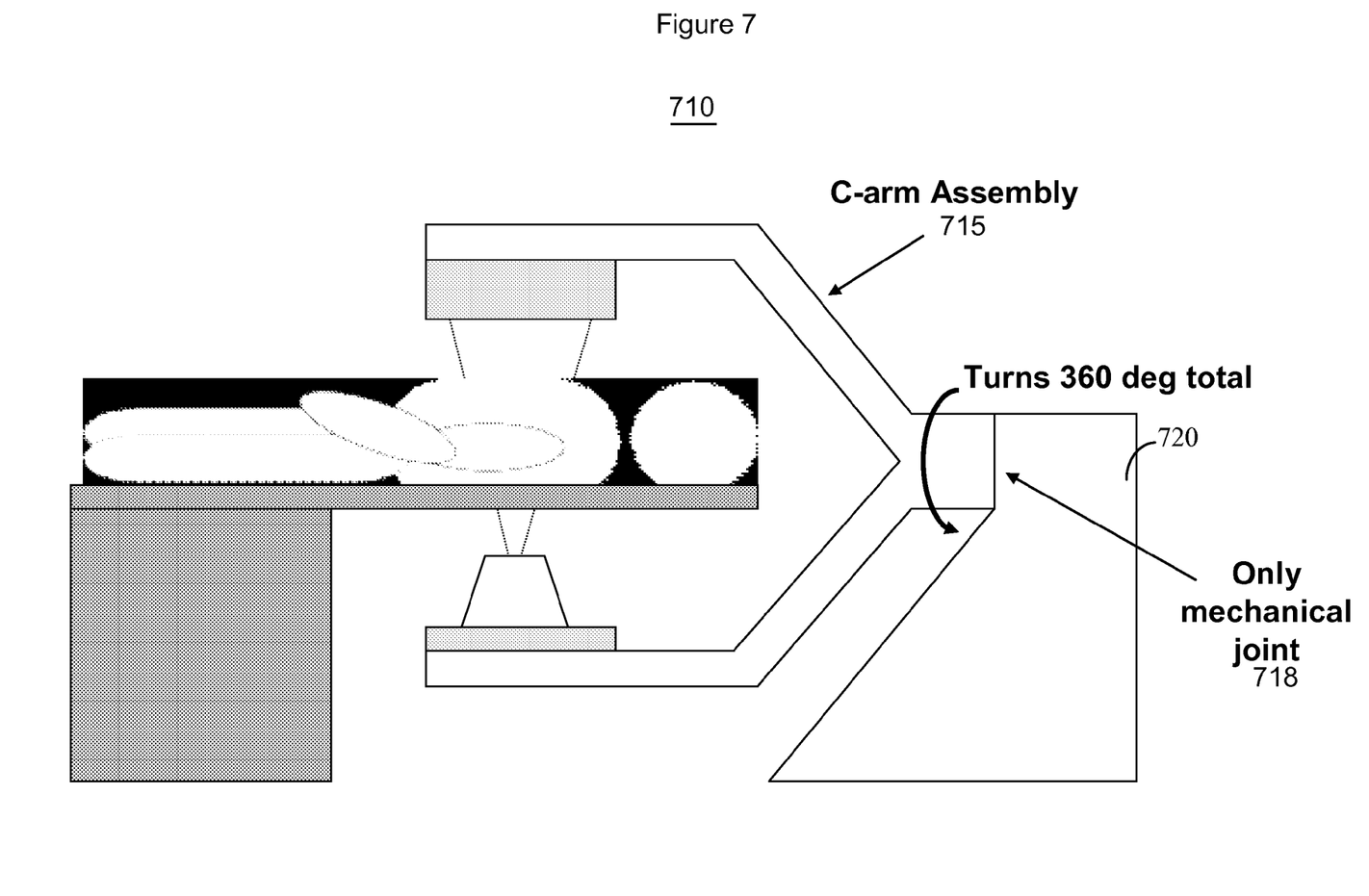
FIG. 7 shows a reduced complexity X-ray C-arm imaging system providing reduced rate and constrained range rotation, according to invention principles.

FIG. 7 shows a more general-purpose diagnostic scanner for vascular diagnosis comprising reduced complexity X-ray C-arm imaging system 710 providing reduced rate and constrained range rotation. System 710 uses C-arm assembly 715 advantageously having a single 360 degree rotation joint 718 connecting assembly 715 to stand 720. System 710 advantageously employs single joint 718 having a single degree of freedom enabling a reduced cost complexity imaging system providing 360 degree imaging capability using C-arm Assembly 715 comprising a rigid object. Thereby system 710 has reduced complexity construction and cost facilitating accurate system calibration and improved reliability. The system advantageously employs a long half-life contrast agent enabling an increased number of projection images to be acquired for 3D reconstruction using closer angular spacing than a known imaging system since the longer persistence contrast agent enables capture of an image at a reduced rate such as once per cardiac cycle, for example. The long persistence contrast agent also provides substantially constant contrast agent concentration in patient anatomy for a duration in excess of 20 minutes. The capture speed requirement of an imaging detector need not be changed. A known C-arm system typically requires higher cost construction involving multiple degrees of freedom of movement. Further, known flat panel image detector systems are typically limited to 60 frames per second, which constrains the number of images that can be captured during a contrast bolus.

Further, system 710 uses a long persistence contrast agent to improve contrast agent homogeneity reducing streaming artifacts that affect image quality associated with known contrast agent boluses. System 710 has increased stability and advantageously eliminates need for capability to adjust distance between radiation source and detector and for cranial-caudal movement capability. Also system calibration is more accurate compared to known C-arm systems and improves image quality during the course of image acquisition during which inhomogeneities can occur affecting image quality. System 710 captures images over 360 degrees, which improves image quality whereas known C-arm CT systems capture images over 180 degrees. System 710 also provides Pulse Width optimization for a particular clinical application and provides Focal Spot optimization for a particular clinical application.

Each year over 6 million people present to a hospital emergency department with acute chest pain. Emergency physicians need to rapidly and accurately determine whether a patient is suffering from an emergency medical condition such as acute coronary syndrome (ACS), aortic dissection (AD), or pulmonary embolism (PE). This is a so-called triple-rule out diagnosis and system 710 performs this with a single scan and also provides diagnosis of peripheral artery disease and in-stent restenosis and cerebral 3D angiograms. In one embodiment imaging at multiple angulations is performed, such as cranial and caudal partial sweeps to improve image quality. Further in another embodiment a scout scan is performed to acquire images from a particular location supporting selection of an optimum image.

Figure 8:
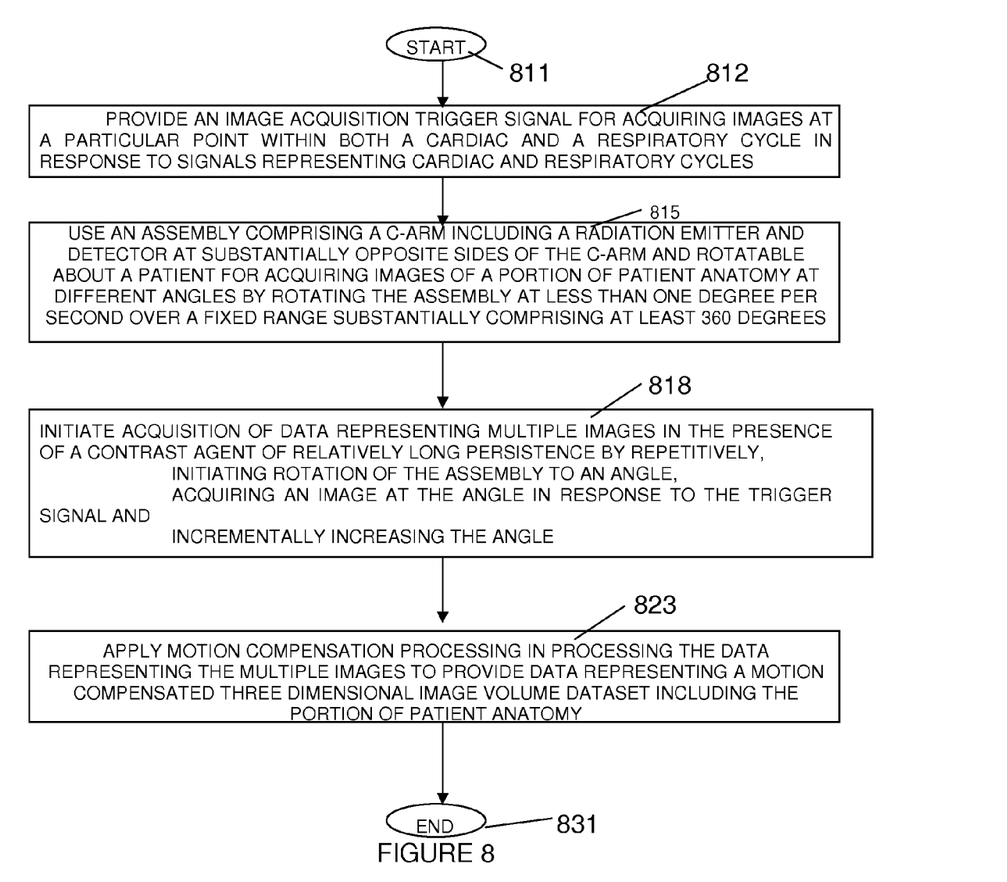
FIG. 8 shows a flowchart of a process performed by a system for acquiring images in the presence of a contrast agent of relatively long persistence, according to invention principles.

FIG. 8 shows a flowchart of a process performed by system 10 (FIG. 1) for acquiring images in the presence of a contrast agent of relatively long persistence. In step 812 following the start at step 811, synchronization processor 28 provides an image acquisition trigger signal for acquiring images at a particular point within both a cardiac and a respiratory cycle in response to signals representing cardiac and respiratory cycles. In step 815, image acquisition device 25 includes an X-ray imaging C-arm assembly comprising a radiation detector 39 and emitter 36 at substantially opposite sides of the C-arm and is rotatable about a patient for acquiring images of a portion of patient anatomy at different angles. The system includes a motor for rotating the assembly at less than one degree per second over a fixed range substantially comprising at least 360 degrees. An extendible and retractable cable enables rotation of the assembly over a fixed range substantially comprising at least 360 degrees. The C-arm in one embodiment is attached to a fixed non-rotating base via a single joint.

In step 818, imaging controller 15 initiates acquisition of data representing multiple images in the presence of a contrast agent of relatively long persistence by repetitively, initiating rotation of the assembly to an angle, acquiring an image at the angle in response to the trigger signal and incrementally increasing the angle. In one embodiment, the C-arm is rotatable about a single axis through patient 11 on patient support table 5 and the C-arm is limited to a single degree of freedom of motion comprising rotation about the single axis. In step 823 image data processor 23 applies a motion compensation function in processing the data representing the multiple images to provide data representing a motion compensated three dimensional image volume dataset including the portion of patient anatomy. Processor 23 applies motion compensation processing using a displacement value calculated based on displacement of radio-opaque markers. The motion compensation includes shifting one image relative to another in response to a determined correction. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A three-dimensional X-ray imaging system uses long persistence contrast agents to reduce mechanical and electrical imaging system hardware and associated complexity using patient ECG and respiration signals to trigger image acquisition over an extended time period when the heart is in the same state of a heart cycle. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both. No claim element herein is to be construed under the provisions of 35 U.S.C. 112, sixth paragraph, unless the element is expressly recited using the phrase "means for."

What is claimed is:

1. A system for acquiring images in the presence of a contrast agent of relatively long persistence, comprising:
   a synchronization processor for providing an image acquisition trigger signal for acquiring images at a particular point within both a cardiac and a respiratory cycle in response to signals representing cardiac and respiratory cycles;
   an image acquisition device including an assembly comprising a radiation emitter and detector rotatable about a patient for acquiring images of a portion of patient anatomy at different angles; and
   an imaging controller for initiating acquisition of data representing a plurality of images in the presence of a contrast agent of relatively long persistence by repetitively,
      initiating rotation of said assembly to an angle,
      acquiring an image at the angle in response to the trigger signal and
      incrementally increasing the angle.

2. A system according to claim 1, wherein
   said imaging controller, repetitively, for angular rotation encompassing substantially 360 degrees about a patient,
      initiates rotation of said assembly to an angle,
      acquires an image at the angle in response to the trigger signal and
      incrementally increases the angle.

3. A system according to claim 1, including
   an image data processor for processing said data representing said plurality of images to provide data representing a three dimensional image volume dataset including said portion of patient anatomy.

4. A system according to claim 3, including
   an image data processor for applying motion compensation processing in processing said data representing said plurality of images to provide data representing a motion compensated three dimensional image volume dataset including said portion of patient anatomy.

5. A computed tomography X-ray imaging system for acquiring images in the presence of a contrast agent of relatively long persistence, comprising:
   a synchronization processor for providing an image acquisition trigger signal for acquiring images at a particular point within both a cardiac and a respiratory cycle in response to signals representing cardiac and respiratory cycles;
   an image acquisition device including an assembly comprising a radiation emitter and detector rotatable about a patient for acquiring images of a portion of patient anatomy at different angles including a motor for rotating the assembly at less than one degree per second over a fixed range substantially comprising at least 360 degrees; and
   an imaging controller for initiating acquisition of data representing a plurality of images in the presence of a contrast agent of relatively long persistence by repetitively,
      initiating rotation of said assembly to an angle,
      acquiring an image at the angle in response to the trigger signal and
      incrementally increasing the angle.

6. A system according to claim 5, including
   an extendible and retractable cable enabling rotation of the assembly over a fixed range substantially comprising at least 360 degrees.

7. An X-ray imaging system for acquiring images in the presence of a contrast agent of relatively long persistence, comprising:
- a synchronization processor for providing an image acquisition trigger signal for acquiring images at a particular point within both a cardiac and a respiratory cycle in response to signals representing cardiac and respiratory cycles;
- an image acquisition device including an assembly comprising a C-arm including a radiation emitter and detector at substantially opposite sides of said C-arm and rotatable about a patient for acquiring images of a portion of patient anatomy at different angles including a motor for rotating the assembly at less than one degree per second over a fixed range substantially comprising at least 360 degrees, said C-arm being attached to a fixed non-rotating base via a single joint; and
- an imaging controller for initiating acquisition of data representing a plurality of images in the presence of a contrast agent of relatively long persistence by repetitively,
  - initiating rotation of said assembly to an angle,
  - acquiring an image at the angle in response to the trigger signal and
  - incrementally increasing the angle.

8. A system according to claim 7, wherein
said C-arm is rotatable about a single axis, said axis being through a patient on a patient support table.

9. A system according to claim 8, wherein
said C-arm is limited to a single degree of freedom of motion comprising rotation about said single axis.

10. A method for acquiring images in the presence of a contrast agent of relatively long persistence, comprising the steps of:
- providing an image acquisition trigger signal for acquiring images at a particular point within both a cardiac and a respiratory cycle in response to signals representing cardiac and respiratory cycles;
- using an image acquisition device including an assembly comprising a radiation emitter and detector rotatable about a patient for acquiring images of a portion of patient anatomy at different angles; and
- initiating acquisition of data representing a plurality of images in the presence of a contrast agent of relatively long persistence by repetitively,
  - initiating rotation of said assembly to an angle,
  - acquiring an image at the angle in response to the trigger signal and
  - incrementally increasing the angle.

11. A method according to claim 10, including the steps of repetitively, for angular rotation encompassing substantially 360 degrees about a patient,
- initiates rotation of said assembly to an angle,
- acquires an image at the angle in response to the trigger signal and
- incrementally increases the angle.

12. A method according to claim 10, including the step of processing said data representing said plurality of images to provide data representing a three dimensional image volume dataset including said portion of patient anatomy.

13. A method according to claim 12, including the step of applying motion compensation processing in processing said data representing said plurality of images to provide data representing a motion compensated three dimensional image volume dataset including said portion of patient anatomy.

14. A method according to claim 10, including the step of rotating the assembly at less than one degree per second over a fixed range substantially comprising at least 360 degrees.

15. A method according to claim 14, wherein
said assembly comprises a radiation emitter and detector C-arm attached to a fixed non-rotating base via a single joint and
including the step of rotating the C-arm at less than one degree per second over a fixed range substantially comprising at least 360 degrees.

16. A method according to claim 12, including the step of applying motion compensation processing using a displacement calculated based on displacement of radio-opaque markers between first and second images acquired at substantially the same angle of C-arm rotation, the first image being acquired in the absence of contrast agent and the second image being acquired in the presence of contrast agent.

* * * * *